United States Patent
Copeland et al.

(10) Patent No.: US 6,750,359 B1
(45) Date of Patent: Jun. 15, 2004

(54) METHODS FOR TREATING DEODORIZER DISTILLATE

(75) Inventors: Dick Copeland, Omaha, NE (US); W. Maurice Belcher, Omaha, NE (US)

(73) Assignee: IP Holdings, L.L.C., Omaha, NE (US)

( * ) Notice: Subject to any disclaimer, the term of this patent is extended or adjusted under 35 U.S.C. 154(b) by 398 days.

(21) Appl. No.: 09/946,810

(22) Filed: Sep. 4, 2001

(51) Int. Cl.⁷ .................................................. C11B 1/00
(52) U.S. Cl. ........................................ 554/205; 422/800
(58) Field of Search ........................... 554/205; 422/800

(56) References Cited

U.S. PATENT DOCUMENTS

| | | | |
|---|---|---|---|
| 2,349,270 A | 5/1944 | Hickman | |
| 2,410,926 A | 11/1946 | Bush et al. | |
| 2,621,196 A | 12/1952 | Thurman | |
| 3,153,055 A | 10/1964 | Brown et al. | |
| 3,239,547 A | 3/1966 | Brion et al. | |
| 3,369,344 A | 2/1968 | Jackson et al. | |
| 4,036,865 A | 7/1977 | Hartmann et al. | |
| 4,049,686 A | 9/1977 | Ringers et al. | |
| 4,072,482 A | 2/1978 | Aoki et al. | |
| 4,240,972 A | 12/1980 | Mag et al. | |
| 4,698,185 A | 10/1987 | Dijkstra et al. | |
| 4,713,155 A | 12/1987 | Arutjunian et al. | |
| 4,789,554 A | 12/1988 | Scavone et al. | |
| 4,804,555 A | 2/1989 | Marschner et al. | |
| 4,996,072 A | 2/1991 | Marschner et al. | |
| 5,424,457 A | 6/1995 | Sumner, Jr. et al. | |
| 5,436,018 A | 7/1995 | Massie et al. | |
| 5,487,817 A | 1/1996 | Fizet | |
| 5,696,278 A | 12/1997 | Segers | |
| 6,172,248 B1 | 1/2001 | Copeland et al. | |
| 2002/0169333 A1 * | 11/2002 | Kellens et al. | .............. 554/205 |

FOREIGN PATENT DOCUMENTS

| | | |
|---|---|---|
| DE | 723436 | 6/1942 |
| GB | 701633 | 12/1953 |
| GB | 714160 | 8/1954 |
| LU | 60116 | 12/1969 |
| NL | 18441 | 8/1928 |
| NL | 6805527 | 10/1968 |
| WO | WO 86/04603 | 8/1986 |
| WO | WO 94/12596 | 6/1994 |
| WO | WO 96/41852 | 12/1996 |

OTHER PUBLICATIONS

Patent Abstract of Japan, vol. 1997, No. 10, Oct. 31, 1997, JP 09 154504 (Asahi Denka Kogyo KK), Jun. 17, 1997.
International Search Report for PCT/US02/27471 (2 pages).

* cited by examiner

*Primary Examiner*—Deborah D. Carr
(74) *Attorney, Agent, or Firm*—McDonnell Boehnen Hulbert & Berghoff

(57) ABSTRACT

This invention relates to methods for treating distillates obtained during the process of deodorizing various oils. More particularly, this invention relates to methods for recovering fatty acids, tocopherols, and sterols from a distillate obtained from the deodorizing of various oils.

17 Claims, 1 Drawing Sheet

METHODS FOR TREATING DEODORIZER DISTILLATE

FIELD OF THE INVENTION

This invention relates to methods for treating distillates obtained during the process of deodorizing various oils. More particularly, this invention relates to methods for recovering fatty acids, tocopherols, and sterols from a distillate obtained from the deodorizing of various oils.

BACKGROUND OF THE INVENTION

Oils derived from plants and animals are valuable sources of fatty acids, tocopherols, and sterols. During the process of refining such oils, however, significant amounts of these components, especially the tocopherols and sterols, are lost to various intermediate byproducts and waste streams, which include acidulated soapstocks, deodorizer distillates, or both, depending on the refining method selected. Accordingly, numerous methods have been proposed for recovering fatty acids, tocopherols, and sterols from various refining intermediates, including deodorizer distillates that are obtained as byproducts of a high-temperature distillation step (commonly termed deodorization) during the production of oils and fats.

Deodorization is usually the final step in producing oils and fats from plant and animal sources. Vegetable oils such as soybean oil typically contain volatile impurities that can impart objectionable odor and taste. These volatile compounds generally must be removed to produce edible oils. Deodorization generally involves a steam stripping process wherein steam is contacted with oil in a distillation apparatus operating at low pressure and a temperature sufficient to vaporize objectionable volatile impurities at the operating pressure. This process, commonly known as vacuum-steam deodorization, relies upon volatility differences between the oil and the objectionable impurities to strip the relatively more volatile objectionable impurities from the relatively less volatile oil. In a typical vacuum-steam deodorizing process, vegetable oil is introduced into a distillation apparatus having a plurality of vertically spaced trays, commonly termed stripping trays. Within each stripping tray, steam injected into the vegetable oil entrains objectionable volatile impurities. The combined steam and entrained distillation vapors are usually collected and condensed to form a distillate that can be disposed of or processed further to recover valuable materials.

The major constituents of deodorizer distillates are fatty acids, tocopherols, and sterols, which are present in various relative amounts depending on the oil source and the refining steps the oil is subjected to prior to deodorization. Deodorizer distillate itself has a certain commercial value. However, greater value can be realized when deodorizer distillate is split into a fatty acid-enriched fraction and a fraction enriched in sterols and tocopherols.

Fatty acids isolated from deodorizer distillates are utilized in several nonfood applications and are particularly useful as fluidizing agents for lecithin. Such fatty acids also can be utilized as precursors in a wide variety of molecular synthesis schemes. Typically, the fatty acid portion of deodorizer distillate comprises $C_{10}$–$C_{22}$ saturated and unsaturated fatty acids. Soybean deodorizer distillate in particular contains about 50 percent by weight fatty acids.

Deodorizer distillates also contain sterols, which are valuable precursors in the production of hormones. Stigmasterol is used in manufacturing progesterone and corticoids. Sitosterol is used to produce estrogens, contraceptives, diuretics, and male hormones. Soybean deodorizer distillate in particular contains from about 10 to about 18 percent by weight total sterols, of which about 50% is sitosterol, about 20% is stigmasterol, about 20% is campesterol, and about 10% is other minor sterols.

The final major component of deodorizer distillates is tocopherol. Tocopherols are valuable natural antioxidants that help prevent oxidation and spoilage. Tocopherols are also utilized in the production of Vitamin E. Distillates obtained from soybean oil deodorization generally contain a mixture of $\alpha$, $\beta$, $\gamma$, and $\delta$ tocopherol isomers in a ratio of about 15:5:30:50. Alpha tocopherol has the most powerful biological Vitamin E activity. The other tocopherols have weaker Vitamin E activity but stronger antioxidant activity. If maximum Vitamin E activity is desired, non-alpha tocopherols can be converted into the alpha form by well-known techniques, such as methylation.

In the past, recovering tocopherols and sterols from deodorizer distillates and related mixtures has proved complicated and expensive. One difficulty associated with isolating one or more distillate fractions enriched in fatty acids, tocopherols, and/or sterols from deodorizer distillates is that the boiling points of sterols and tocopherols are roughly in the same range. Another difficulty is that deodorizer distillate can undergo thermal degradation if it is processed for extended periods at the temperatures at which sterols and tocopherols vaporize, such temperature conditions which can cause fatty acids to convert into undesirable trans isomeric forms.

Numerous methods have been proposed for treating deodorizer distillates to isolate and recover one or more components. In many of these methods, a first essential process step involves subjecting the fatty acids to an esterification or saponification reaction. For example, U.S. Pat. No. 3,153,055 teaches a process for isolating sterols and tocopherols from deodorizer distillate by esterifying the fatty acids with a monohydric alcohol under strongly acidic conditions. The sterols and tocopherols are then fractionally extracted from the esterification product mixture with a combination of polar and nonpolar solvents.

In an alternative esterification method, U.S. Pat. No. 5,487,817 teaches esterifying the sterols with the fatty acids and then distilling the resulting mixture to obtain a residue containing sterol esters and a distillate containing tocopherols. Sterols are then isolated from the residue by subjecting the sterol esters to cleavage under acidic conditions.

U.S. Pat. No. 2,349,270 discloses that deodorizer distillate can be treated with lime soap to saponify the fatty acids, followed by extraction of the unsaponifiable fraction (tocopherols and sterols) with acetone, in which the saponification products are insoluble. The extract is then washed and concentrated, as for example by solvent distillation, and then cooled to crystallize sterols which are removed by filtration, leaving a high purity tocopherol fraction. The fatty acid soaps formed by the process can be acidulated and converted into free fatty acids.

Extractive separation methods also have been employed in treating deodorizer distillates to isolate one or more components. For example, U.S. Pat. No. 5,138,075 describes a method for recovering tocopherols from a deodorized distillate which comprises contacting the distillate with liquid water at elevated temperature and pressure, thereby producing a raffinate phase stream having a relatively high concentration of tocopherols and an extract phase stream having a relatively high concentration of fatty acids.

The raffinate stream and the extract stream are then cooled to a temperature at which the organic components thereof are immiscible with liquid water, whereupon removal of water produces a tocopherol-enriched fraction and a fatty acid-enriched fraction, respectively.

None of the above methods for isolating one or more components from a deodorizer distillate has proved satisfactory, however. Methods employing an esterification step or saponification step introduce processing complexity and require later processing steps that often involve use of strong mineral acids in order to convert the respective esters or soaps into free sterols and free fatty acids. Mineral acids can be dangerous in handling and can induce discoloration or other degradation of distillate components. Methods requiring extractive steps are expensive and create the potential for contamination by residual solvent.

Previously known methods for isolating one or more components from a deodorizer distillate generally have required lengthy and costly processing steps. Consequently, further improvements in methods for treating deodorizer distillates have been sought. The present invention relates to improved processes having advantages over those previously disclosed. The methods of the invention produce a fatty acid-enriched distillate fraction directly and simply from a vaporized distillate. The methods of the invention also produce a distillate fraction enriched in sterols and tocopherols, which can be treated further by various methods to isolate a sterol fraction and a tocopherol fraction.

SUMMARY OF THE INVENTION

One aspect of the present invention relates to methods for isolating one or more components from vaporized distillates obtained from the deodorization of various oils.

Another aspect of the present invention relates to methods for producing mixtures enriched in free fatty acids from distillates obtained from the deodorization of various oils.

Yet another aspect of the invention relates to methods for producing mixtures enriched in sterols and tocopherols from distillates obtained from the deodorization of various oils.

One embodiment of the invention is a process for isolating components from a vaporized distillate that comprises the steps of introducing a vaporized distillate comprising sterols, tocopherols, and fatty acids into a first condensing zone of a condensing unit having at least two condensing zones and operating at a pressure of less than about 10 mm Hg, the first condensing zone operating at a temperature of from about 330 to about 450° F.; condensing a first fraction of the vaporized distillate in the first condensing zone to produce a first condensate enriched in sterols and tocopherols, leaving a remaining fraction of vaporized distillate; introducing the remaining fraction of vaporized distillate into a second condensing zone of the condensing unit, the second condensing zone operating at a temperature of from about 100 to about 170° F.; and condensing a second fraction of the remaining fraction of vaporized distillate in the second condensing zone to produce a second condensate enriched in fatty acids, leaving a waste vapor.

Another embodiment of the invention is a process for isolating components from a vaporized distillate that comprises the steps of introducing a vaporized distillate comprising sterols, tocopherols, and fatty acids into a first condensing zone of a condensing unit having at least two condensing zones and operating at a pressure of less than about 10 mm Hg, the first condensing zone operating at a temperature of from about 330 to about 450° F.; condensing a first fraction of the vaporized distillate in the first condensing zone to produce a first condensate enriched in sterols and tocopherols, leaving a remaining fraction of vaporized distillate; introducing the remaining fraction of vaporized distillate into a second condensing zone of the condensing unit, the second condensing zone operating at a temperature of from about 100 to about 170° F.; condensing a second fraction of the remaining fraction of vaporized distillate in the second condensing zone to produce a second condensate enriched in fatty acids, leaving a waste vapor; recovering the first condensate; and recovering the second condensate.

Yet another embodiment of the invention is a process for isolating components from a vaporized distillate that comprises the steps of introducing a vaporized distillate comprising sterols, tocopherols, and fatty acids into a first condensing zone of a condensing unit having at least two condensing zones and operating at a pressure of less than about 10 mm Hg, the first condensing zone operating at a temperature of from about 330 to about 450° F.; condensing a first fraction of the vaporized distillate in the first condensing zone to produce a first condensate enriched in sterols and tocopherols by passing the vaporized distillate through a first packing where it is contacted with recycled first condensate maintained at a temperature of about 380° F., leaving a remaining fraction of vaporized distillate; introducing the remaining fraction of vaporized distillate into a second condensing zone of the condensing unit, the second condensing zone operating at a temperature of from about 100 to about 170° F.; and condensing a second fraction of the remaining fraction of vaporized distillate in the second condensing zone to produce a second condensate enriched in fatty acids by passing the remaining fraction of vaporized distillate through a second packing where it is contacted with recycled second condensate maintained at a temperature of about 135° F., leaving a waste vapor.

A further embodiment of the invention is a process for isolating components from a vaporized distillate that comprises the steps of introducing a vaporized distillate comprising sterols, tocopherols, and fatty acids into a first condensing zone of a condensing unit having at least two condensing zones and operating at a pressure of less than about 10 mm Hg, the first condensing zone operating at a temperature of from about 330 to about 450° F.; condensing a first fraction of the vaporized distillate in the first condensing zone to form a first condensate enriched in sterols and tocopherols by passing the vaporized distillate through a first packing where it is contacted with recycled first condensate maintained at a temperature of about 380° F., leaving a remaining fraction of vaporized distillate; introducing the remaining fraction of vaporized distillate into a second condensing zone of the condensing unit, the second condensing zone operating at a temperature of from about 100 to about 170° F.; condensing a second fraction of the remaining fraction of vaporized distillate in the second condensing zone to produce a second condensate enriched in fatty acids by passing the remaining fraction of vaporized distillate through a second packing where it is contacted with recycled second condensate maintained at a temperature of about 135° F., leaving a waste vapor; recovering the first condensate; and recovering the second condensate.

These and other aspects of the invention will become apparent in light of the detailed description below.

BRIEF DESCRIPTION OF THE DRAWINGS

The patent or application file contains at least one drawing executed in color. Copies of this patent or patent application publication with color drawing(s) will be provided by the office upon request and payment of the accessory fee.

DESCRIPTION OF A PREFERRED EMBODIMENT

Figure 1:
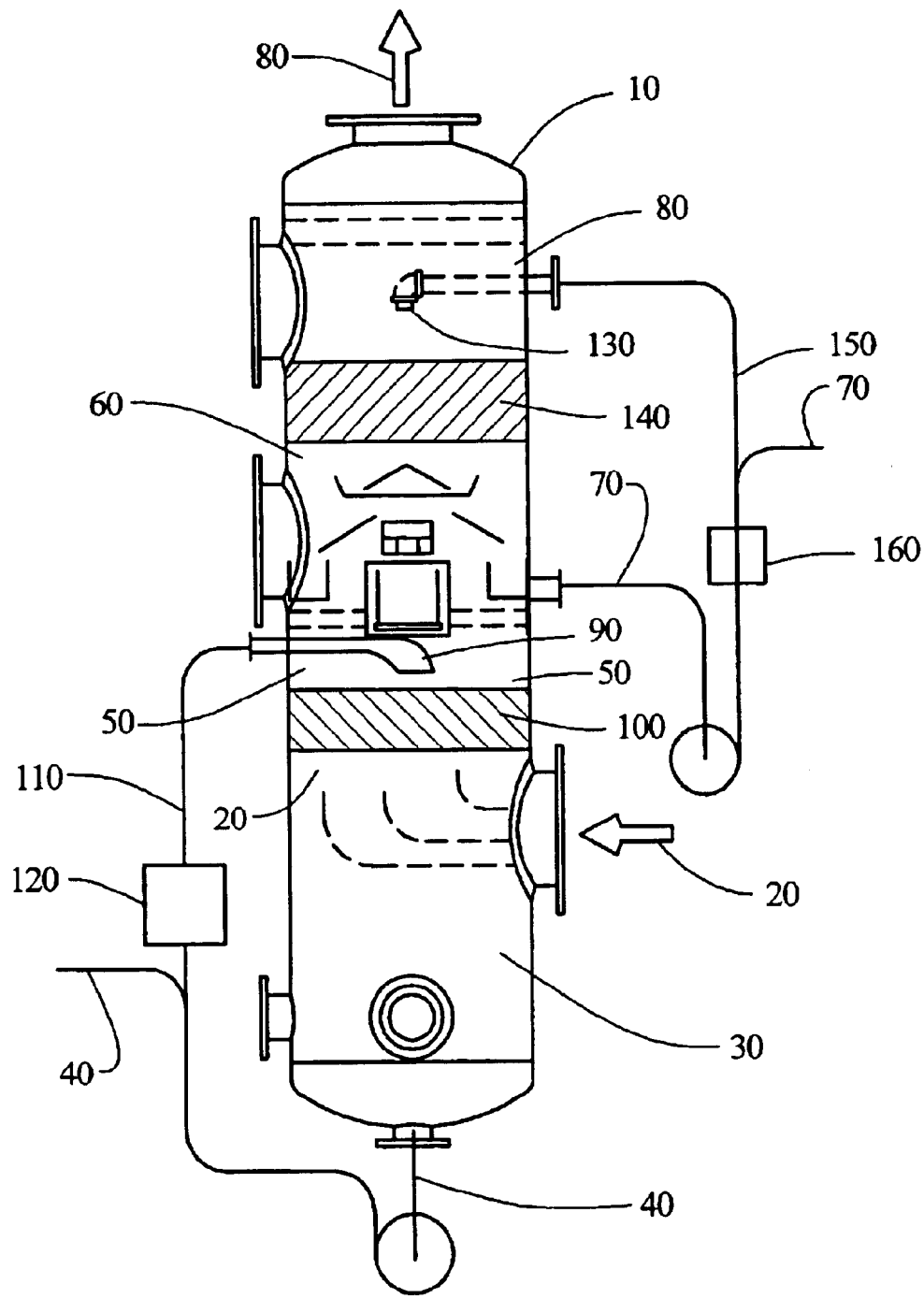
FIG. 1 is a side elevational view of a scrubber suitable for carrying out the processes of the present invention and illustrating the flow path of the various vapor and condensate streams utilized and/or produced therein.

Reference numeral 10 of FIG. 1 generally indicates a condensing unit suitable for carrying out the processes of the invention. As illustrated in FIG. 1, the improved processes of the invention for isolating components from deodorizer distillates generally entail introducing a vaporized distillate 20 comprising sterols, tocopherols, and fatty acids into a first condensing zone 30 of a condensing unit 10 having at least two condensing zones and operating at a pressure of less than about 10 mm Hg, the first condensing zone 30 operating at a temperature of from about 330 to about 450° F.; condensing a first fraction of the vaporized distillate 20 in the first condensing zone 30 to produce a first condensate 40 enriched in sterols and tocopherols, leaving a remaining fraction of vaporized distillate 50; introducing the remaining fraction of vaporized distillate 50 into a second condensing zone 60 of the condensing unit 10, the second condensing zone 60 operating at a temperature of from about 100 to about 170° F.; and condensing a second fraction of the remaining fraction of vaporized distillate 50 in the second condensing zone 60 to produce a second condensate 70 enriched in fatty acids, leaving a waste vapor 80. The improved processes of the invention can be conducted as batch, semi-continuous, or continuous processes.

The improved processes of the invention serve to isolate the components of vaporized distillates obtained from the deodorization of various oils. Many such distillates are suitable for use in the invention, including but not limited to those obtained from the deodorization of soybean oil, corn oil, cottonseed oil, palm oil, peanut oil, rapeseed oil, safflower oil, sunflower seed oil, sesame seed oil, rice bran oil, coconut oil, canola oil, and mixtures thereof. A particularly suitable distillate is soybean deodorizer distillate.

The composition of deodorizer distillates will vary depending upon the oil type and pre-deodorization refining history. Distillate obtained from the deodorization of alkali-refined soybean oil generally contains about 50 percent by weight fatty acids, about 15 percent by weight tocopherols, and about 18 percent by weight sterols. Distillate resulting from the deodorization of physically refined soybean oil usually comprises about 70 percent by weight fatty acids, about 9 percent by weight tocopherols, and about 11 percent by weight sterols. Distillate obtained from the deodorization of soybean oil refined via an organic acid refining process, as disclosed in U.S. Pat. No. 6,172,248, herein incorporated by reference, typically contains about 55 percent by weight fatty acids, about 12 percent by weight tocopherols, and about 14 percent by weight sterols. Any of these deodorizer distillates, concentrated forms of such distillates, or mixtures thereof are suitable for use in the present invention. Such distillates are best provided in vaporized form in order to minimize the risk of thermal degradation that can occur when a distillate is allowed to cool into a condensate and is then reheated for further processing. Generally, distillate coming from the deodorizer has a temperature of about 300° F. and is at a pressure of about 2 to 6 mm Hg.

The vaporized distillate 20 is introduced into a first condensing zone 30 of a condensing unit 10 having at least two condensing zones and operating at a pressure of less than about 10 mm Hg. The condensing unit 10 can be any piece of equipment capable of operating at reduced pressure and elevated temperature and having at least two condensing zones. Preferably, the condensing unit 10 is a scrubber fabricated or adapted to contain at least two condensing zones. Reduced pressure can be generated by any convenient source. Steam jet ejector systems are commonly employed. Most preferred is to use a Nash-Kinema three-stage vacuum system or a two-stage vacuum system plus a vacuum pump. With a three-stage ejector system, the usual vacuum generated in the condensing unit will be from about 4 to about 6 mm Hg. Preferably, the condensing unit 10 operates at a pressure of less than about 6 mm Hg. Most preferably, the condensing unit 10 operates at a pressure of less than about 4 mm Hg.

The first condensing zone 30 operates at a temperature less than the boiling point of tocopherols and sterols at the operating temperature but greater than the boiling point of fatty acids at the operating pressure. Table 1 indicates the boiling point of tocopherols and sterols at several reduced pressures.

TABLE 1

| Pressure (mm Hg) | Tocopherols boiling point (° F.) | Sterols boiling point (° F.) |
| --- | --- | --- |
| 1 | 450 | 470 |
| 2 | 470 | 475 |
| 3 | 490 | 505 |
| 4 | 500 | 520 |

At each of the pressures listed in Table 1, the boiling point of fatty acids is less than 200 ° F. Generally, the first condensing zone 30 operates at a temperature of from about 330 to about 450° F. Preferably, the first condensing zone 30 operates at a temperature of from about 355 to about 405° F. Most preferably, the first condensing zone 30 operates at a temperature of from about 370 to about 390° F.

Within the first condensing zone 30, a first fraction of the vaporized distillate 20 is condensed to produce a first condensate 40 enriched in sterols and tocopherols, which can be recovered and profitably sold or processed further. Remaining uncondensed vaporized distillate, termed herein as a remaining fraction of vaporized distillate 50, flows to a second condensing zone 60 for further processing. Generally, the first condensate 40 is obtained in an amount of about 50 weight percent of the vaporized distillate 20. The first condensate 40 generally comprises about 5 percent by weight fatty acids, about 25 percent by weight tocopherols, and about 30 percent by weight sterols. Optionally, a level controller in the bottom of the first condensing zone 30 maintains a constant volume of the first condensate 40 in the system, with the excess drawn off and sent to storage or subsequent processing steps.

Generally, at least a portion of the first condensate 40 is recirculated into the first condensing zone 30 through a spray nozzle 90 as a mist or spray countercurrent to the flow direction of the vaporized distillate 20 to provide direct cooling upon contact with vaporized distillate 20 as it passes upward. Optionally, condensation of a portion of the vaporized distillate 20 in the first condensing zone 30 occurs by passing the vaporized distillate 20 through a first packing 100 where it is contacted with recycled first condensate 110 maintained at a temperature of about 380° F. by circulating through a heat exchanger 120.

The use of packing substantially increases the surface area in which recycled first condensate and vaporized distillate can interact. The packing itself also provides an additional source of cooling, since it tends to acquire the temperature of the recycled first condensate. The type of packing is selected based on factors well known to those in the art, including mechanical strength, resistance to corrosion, cost, capacity, and efficiency. The packing may take the form of a stainless steel grid or mesh, porcelain or ceramic rings or saddles, or other suitable inert materials. Preferably, first packing 100 comprises a plurality of sawtooth-profile stainless steel plates spaced closely apart and perforated by a plurality of holes. The amount of the first packing 100 used depends upon the cross-sectional area of the first condensing zone 30, the maximum desired pressure drop, the flow rate of vaporized distillate 20, and the desired percentage conversion of vaporized distillate to first condensate. Generally, for a first condensing zone 30 having a 42-inch diameter circular cross-sectional area, about 15 vertical inches of first packing 100 are utilized, and the first packing 100 extends substantially throughout the entire cross-sectional area of the first condensing zone 30.

The remaining fraction of vaporized distillate 50 exiting the first condensing zone 30 enters the second condensing zone 60 of the condensing unit 10, where a second fraction of the remaining fraction of vaporized distillate 50 is condensed into a second condensate 70 enriched in fatty acids, leaving a waste vapor 80. The second condensing zone 60 operates at a temperature less than the boiling point of fatty acids at the operating pressure. Generally, the second condensing zone 60 operates at a temperature of from about 100 to about 170° F. Preferably, the second condensing zone 60 operates at a temperature of from about 125 to about 145° F. Most preferably, the second condensing zone 60 operates at a temperature of from about 130 to about 140° F.

Within the second condensing zone 60, a second fraction of the remaining fraction of vaporized distillate 50 is condensed to produce a second condensate 70 enriched in fatty acids, which can be recovered and profitably sold. The remaining waste vapor 80, flows to the vacuum system. Generally, the second condensate 70 is obtained in an amount of about 50 weight percent of the original vaporized distillate 20. The second condensate 70 generally comprises about 90 percent by weight fatty acids, and only trace amounts of sterols and tocopherols. Optionally, a level controller in the bottom of the second condensing zone 60 maintains a constant volume of the second condensate 70 in the system, with the excess drawn off and sent to storage.

Generally, at least a portion of the second condensate 70 is recirculated into the second condensing zone 60 through a spray nozzle 130 as a mist or spray countercurrent to the flow direction of the remaining fraction of vaporized distillate 50 to provide direct cooling upon contact with remaining fraction of vaporized distillate 50 as it passes upward. Optionally, condensation of the remaining fraction of vaporized distillate 50 in the second condensing zone 60 occurs by passing the remaining fraction of vaporized distillate 50 through a second packing 140 where it is contacted with recycled second condensate 150 maintained at a temperature of about 135° F. by circulating through a heat exchanger 160. The second packing 140 may take the same form as the first packing 100 or it can be different. Preferably, the second packing 140 is the same material and has the same configuration as the first packing 100.

Once produced, the second condensate 70 can be processed further by various known methods to isolate a sterol and/or a tocopherol fraction. For example, because tocopherols are very soluble in lower aliphatic alcohols such as methanol, whereas sterols are substantially insoluble in such alcohols when cool, the second condensate can be washed in methanol and then filtered to produce an insolubles fraction containing sterols and a filtrate containing tocopherols, which in turn can be distilled to remove methanol. Alternatively, the second condensate can be combined with an adsorption solvent and then passed through a basic anion exchange resin, where tocopherols are selectively adsorbed on the resin and sterols pass through. Adsorbed tocopherols then can be eluted from the resin by passing an eluent phase such as acetic acid through the resin.

All documents, e.g., patents, journal articles, and textbooks, cited above or below are hereby incorporated by reference in their entirety.

One skilled in the art will recognize that modifications may be made in the present invention without deviating from the spirit or scope of the invention. The invention is illustrated further by the following examples, which are not to be construed as limiting the invention in spirit or scope to the specific procedures or compositions described therein.

EXAMPLE 1

A vaporized distillate obtained from the deodorization of Organic refined soybean oil and having a temperature of about 300° F. was directed at a rate of 250,000 pounds per hour into the first condensing zone of a scrubber adapted to contain two condensing zones and operating at a pressure of about 4 mm Hg. The deodorizer distillate comprised about 50 percent by weight fatty acids, about 12 percent by weight tocopherols, about 14 percent by weight sterols, and about 24 percent by weight other components, including oil.

The scrubber comprised a cylindrical tower 14 feet in height and 42 inches in diameter. The first condensing zone was about 4 feet in height and contained 15 vertical inches of packing. The packing in the first condensing zone comprised a plurality of sawtooth-profile stainless steel plates spaced closely apart and perforated by a plurality of holes. A spray nozzle extended into the first condensing zone above the packing. Vacuum was supplied to the scrubber by a Nash-Kinema three-stage vacuum system or vacuum pump.

A first fraction comprising about 50 percent by weight of the vaporized distillate entering the first condensing zone was condensed to form a first condensate containing about 5 percent by weight fatty acids, about 25 percent by weight tocopherols, and about 30 percent by weight sterols. Vaporized distillate entering the first condensing zone passed upwards and contacted the packing and recycled first condensate exiting the spray nozzle countercurrent to the flow direction of the vaporized distillate. Recycled first condensate was maintained at a temperature of about 380° F. by passing it through a heat exchanger. The portion of first condensate not used for recycle was continuously withdrawn and sent to storage.

That portion of the vaporized distillate not condensed in the first condensing zone, termed herein as a remaining fraction of vaporized distillate, passed upward into a second condensing zone. The second condensing zone was similar in dimension and configuration compared to the first condensing zone. A second fraction comprising about 50 percent by weight of the original vaporized distillate was condensed in the second condensing zone to form a second condensate containing about 90 percent by weight fatty acids, about 4 percent by weight tocopherols, and about 6 percent by weight sterols. Vapor entering the second condensing zone passed upwards and contacted the packing and recycled second condensate exiting the spray nozzle countercurrent to the flow direction of the vaporized distillate. Recycled second condensate was maintained at a temperature of about 135° F. by passing it through a heat exchanger. The portion of second condensate not used for recycle was continuously withdrawn and sent to storage.

The chain length distribution of fatty acids in the second condensate was as follows:

| %C16:0 | 15–26 |
| %C18:0 | 13–22 |
| %C18:1 | 20–29 |
| %C18:2 | 28–38 |
| %C18:3 | 2–8 |

EXAMPLE 2

A vaporized distillate obtained from the deodorization of conventionally refined soybean oil and having a temperature of about 330° F. was directed at a rate of 25,000 pounds per hour into the first condensing zone of a scrubber adapted to contain two condensing zones and operating at a pressure of about 2.5 mm Hg. The deodorizer distillate comprised about 45 percent by weight fatty acids, about 15 percent by weight tocopherols, about 20 percent by weight sterols, and about 20 percent by weight other components, including oil.

The scrubber comprised a cylindrical tower 18 feet in height and 60 inches in diameter. The first condensing zone was about 5 feet in height and contained 24 vertical inches of packing. The packing in the first condensing zone comprised a plurality of sawtooth-profile stainless steel plates spaced closely apart and perforated by a plurality of holes. A spray nozzle extended into the first condensing zone above the packing. Vacuum was supplied to the scrubber by a Nash-Kinema three-stage vacuum system or vacuum pump.

A first fraction comprising about 55 percent by weight of the vaporized distillate entering the first condensing zone was condensed to form a first condensate containing about 3 percent by weight fatty acids, about 30 percent by weight tocopherols, and about 35 percent by weight sterols. Vaporized distillate entering the first condensing zone passed upwards and contacted the packing and recycled first condensate exiting the spray nozzle countercurrent to the flow direction of the vaporized distillate. Recycled first condensate was maintained at a temperature of about 380° F. by passing it through a heat exchanger. The portion of first condensate not used for recycle was continuously withdrawn and sent to storage.

That portion of the vaporized distillate not condensed in the first condensing zone, termed herein as a remaining fraction of vaporized distillate, passed upward into a second condensing zone. The second condensing zone was similar in dimension and configuration compared to the first condensing zone. A second fraction comprising about 45 percent by weight of the original vaporized distillate was condensed in the second condensing zone to form a second condensate containing about 95 percent by weight fatty acids, about 2 percent by weight tocopherols, and about 3 percent by weight sterols. Vapor entering the second condensing zone passed upwards and contacted the packing and recycled second condensate exiting the spray nozzle countercurrent to the flow direction of the vaporized distillate. Recycled second condensate was maintained at a temperature of about 135° F. by passing it through a heat exchanger. The portion of second condensate not used for recycle was continuously withdrawn and sent to storage.

The chain length distribution of fatty acids in the second condensate was as follows:

| %C16:0 | 15–26 |
| %C18:0 | 13–22 |
| %C18:1 | 20–29 |
| %C18:2 | 28–38 |
| %C18:3 | 2–8 |

The invention and the manner and process of making and using it, are now described in such full, clear, concise and exact terms as to enable any person skilled in the art to which it pertains, to make and use the same. Although the foregoing describes preferred embodiments of the present invention, modifications may be made therein without departing from the spirit or scope of the present invention as set forth in the claims. To particularly point out and distinctly claim the subject matter regarded as invention, the following claims conclude this specification.

What we claim is:

1. A process for isolating components from a vaporized distillate, comprising:
   (a) introducing a vaporized distillate comprising sterols, tocopherols, and fatty acids into a first condensing zone of a condensing unit having at least two condensing zones and operating at a pressure of less than about 10 mm Hg, the first condensing zone operating at a temperature of from about 330 to about 450° F.;
   (b) condensing a first fraction of the vaporized distillate in the first condensing zone to produce a first condensate enriched in sterols and tocopherols, leaving a remaining fraction of vaporized distillate;
   (c) introducing the remaining fraction of vaporized distillate into a second condensing zone of the condensing unit, the second condensing zone operating at a temperature of from about 100 to about 170° F.; and
   (d) condensing a second fraction of the remaining fraction of vaporized distillate in the second condensing zone to produce a second condensate enriched in fatty acids, leaving a waste vapor.

2. The process of claim 1, wherein the first condensing zone operates at a temperature of from about 355 to about 405° F.

3. The process of claim 1, wherein the first condensing zone operates at a temperature of from about 370 to about 390° F.

4. The process of claim 1, wherein the second condensing zone operates at a temperature of from about 125 to about 145° F.

5. The process of claim 1, wherein the second condensing zone operates at a temperature of from about 130 to about 140° F.

6. The process of claim 1, further comprising step (e) recovering the first condensate.

7. The process if claim 1, further comprising step (e) recovering the second condensate.

8. The process of claim 7, further comprising step (f) recovering the second condensate.

9. The process of claim 1, wherein step (b) condensing occurs by passing the vaporized distillate through a first packing where it is contacted with recycled first condensate maintained at a temperature of about 380° F.

10. The process of claim 9, wherein the first packing comprises a plurality of stainless steel plates spaced closely apart and perforated by a plurality of holes.

11. The process of claim 1, wherein step (d) condensing occurs by passing the remaining fraction of vaporized distillate through a second packing where it is contacted with recycled second condensate maintained at a temperature of about 135° F.

12. The process of claim 11, wherein the second packing comprises a plurality of stainless steel plates spaced closely apart and perforated by a plurality of holes.

13. The process of claim 9, wherein wherein step (d) condensing occurs by passing the remaining fraction of vaporized distillate through a second packing where it is contacted with recycled second condensate maintained at a temperature of about 135° F.

14. The process of claim 13, wherein the first packing comprises a plurality of stainless steel plates spaced closely apart and perforated by a plurality of holes.

15. The process of claim 13, wherein the second packing comprises a plurality of stainless steel plates spaced closely apart and perforated by a plurality of holes.

16. The process of claim 14, wherein the second packing comprises a plurality of stainless steel plates spaced closely apart and perforated by a plurality of holes.

17. The process of claim 1, wherein the condensing unit is a scrubber.

* * * * *